United States Patent
Inukai et al.

(10) Patent No.: US 7,390,300 B2
(45) Date of Patent: Jun. 24, 2008

(54) BLOOD PRESSURE MEASURING APPARATUS

(75) Inventors: Hidekatsu Inukai, Nagoya (JP); Toru Oka, Ichinomiya (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 0 days.

(21) Appl. No.: 11/475,917

(22) Filed: Jun. 28, 2006

(65) Prior Publication Data

US 2007/0016085 A1  Jan. 18, 2007

(30) Foreign Application Priority Data

Jun. 29, 2005  (JP)  ............................. 2005-190468

(51) Int. Cl.
*A61B 5/02* (2006.01)

(52) U.S. Cl. .................. 600/485; 600/500; 600/490; 600/483

(58) Field of Classification Search ................ 600/481, 600/483, 485, 490–503
See application file for complete search history.

(56) References Cited

U.S. PATENT DOCUMENTS

| | | | |
|---|---|---|---|
| 6,547,742 B2 * | 4/2003 | Oka et al. ................... | 600/494 |
| 6,612,993 B2 * | 9/2003 | Narimatsu ................... | 600/500 |
| 6,699,197 B2 * | 3/2004 | Narimatsu ................... | 600/500 |
| 6,827,687 B2 * | 12/2004 | Narimatsu et al. ........... | 600/485 |
| 6,878,272 B2 * | 4/2005 | Kawaguchi ............. | 210/321.65 |
| 7,029,449 B2 * | 4/2006 | Ogura ......................... | 600/500 |
| 2002/0087087 A1 * | 7/2002 | Oka et al. .................... | 600/485 |
| 2003/0004420 A1 * | 1/2003 | Narimatsu ................... | 600/485 |
| 2003/0004422 A1 * | 1/2003 | Narimatsu ................... | 600/500 |
| 2003/0167014 A1 * | 9/2003 | Ogura ......................... | 600/513 |
| 2003/0199776 A1 * | 10/2003 | Narimatsu et al. ........... | 600/494 |
| 2004/0158162 A1 * | 8/2004 | Narimatsu ................... | 600/494 |

FOREIGN PATENT DOCUMENTS

JP  10-066681  3/1998

OTHER PUBLICATIONS

Iketani et al., "Photoplethysmogram (Accelerated Pulse Wave) for Evaluating Degree of Arteriosclerosis by Hypertension", Blood Pressure, vol. 10, No. 6, 2003, pp. 54-60 (English translation attached).

* cited by examiner

*Primary Examiner*—Charles A. Marmor, II
*Assistant Examiner*—Navin Natnithithadha
(74) *Attorney, Agent, or Firm*—Drinker Biddle & Reath LLP

(57) ABSTRACT

A pulse wave is detected in a predetermined location of a living body, and the progressive wave component and reflected wave component are extracted from the pulse wave. The pulse wave propagation time is calculated from the progressive wave component and reflected wave component, and blood pressure is calculated on the basis of this pulse wave propagation time. The use of this method provides blood pressure measuring apparatus capable of continuously measuring blood pressure with a simple method.

10 Claims, 5 Drawing Sheets

BLOOD PRESSURE MEASURING APPARATUS

CLAIM OF PRIORITY

This application claims priority from Japanese Patent Application No. 2005-190468, filed on Jun. 29, 2005, which is hereby incorporated by reference herein.

FIELD OF THE INVENTION

The present invention relates to blood pressure measuring apparatus and, more particularly, to blood pressure measuring apparatus capable of noninvasively continuously measuring blood pressure.

BACKGROUND OF THE INVENTION

It is conventionally known that the time (pulse wave propagation time) required for a pulse wave to propagate between two points in a living body or the pulse wave propagation velocity obtained by dividing the blood vessel length between the two points by the pulse wave propagation time has a correlation with the blood pressure. A method of continuously monitoring the blood pressure by continuously measuring, e.g., the pulse wave propagation time by using this relationship is proposed (e.g., Japanese Patent Laid-Open No. 10-66681).

To measure the pulse wave propagation time, however, pulse waves must be measured in different locations, so the measurement requires a long time. Also, it is sometimes difficult to attach sensors or cuffs for measuring pulse waves to two locations. As described in Japanese Patent Laid-Open No. 10-66681, therefore, an electrocardiogram (ECG) is sometimes used instead of one pulse wave. In this case, time difference between the R wave appearance point of the ECG and the feature point of a pulse wave measured at a fingertip is used as the pulse wave propagation time.

In an operating room or ICU, an ECG and pulse wave (at one location) are normally measured at all times. Accordingly, when the ECG is used as one pulse wave, the pulse wave propagation time can be measured without adding any apparatus, so the method is advantageous in cost and operability.

Unfortunately, the use of an ECG has a problem of the measurement accuracy. That is, an ECG is a signal which represents not a pulse wave but the electrical state change of the heart. There is time difference (preelection period) between the timing at which the electrical state change occurs and the timing at which the heart actually contracts to generate a pulse wave. This preelection period has influence on the pulse wave propagation time to be measured.

If the preelection period is constant, correction is easy. However, the preelection period changes from one person to another, and can change occasionally even in the same person. This presently makes the preejection period hard to correct. Accordingly, it is difficult to obtain results more accurate than when blood pressure is calculated from the propagation time obtained from two pulse waves.

SUMMARY OF THE INVENTION

The present invention has been made in consideration of the problems of the prior art as described above, and has as its object to provide blood pressure measuring apparatus capable of continuously measuring blood pressure by a simple method.

According to the present invention, there is provided a blood pressure measuring apparatus comprising: pulse wave detecting unit adapted to detect a pulse wave in a predetermined location of a living body; extracting unit adapted to extract a progressive wave component and a reflected wave component contained in the pulse wave; pulse wave propagation time calculating unit adapted to calculate a pulse wave propagation time from the progressive wave component and the reflected wave component; and blood pressure calculating unit adapted to calculate blood pressure on the basis of the pulse wave propagation time.

In the present invention having the above arrangement, the pulse wave propagation time is measured using the progressive wave component and reflected wave component of a pulse wave measured in one location, and blood pressure is obtained on the basis of this pulse wave propagation time. This obviates the need to measure pulse waves in two locations, so the measurement is easy. In addition, the pulse wave propagation time is measured on the basis of only a pulse wave. Therefore, it is unnecessary to take account of the influence of the preejection period which is required when an ECG is to be used instead of a pulse wave. As a consequence, accurate measurement results can be obtained.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENT

A preferred embodiment of the present invention will now be described in detail in accordance with the accompanying drawings.

First, the principle of the present invention will be explained below.

The waveform of a pulse wave observed in the aortic root differs from those of pulse waves observed in other locations, and various researches and analyses have been conventionally performed on the pulse wave propagation mechanism. The results are that a waveform corresponding to a measurement location is presumably observed as a waveform formed by superposing a progressive wave component generated by the ejection of blood from the left ventricle and a reflected wave component generated when the progressive wave returns after being reflected by the periphery.

The reflected wave is probably generated when the progressive wave propagates in the blood vessel and returns as it is reflected by a point at which the physical characteristic of the blood vessel changes, e.g., a portion where the blood vessel diameter changes (an impedance mismatching point if the blood vessel is regarded as an electrical circuit). Also, the velocity of a pulse wave (a pressure wave propagating in the blood vessel wall) is much faster than the heart beat. Accordingly, the progressive wave component and reflected wave component contained in a pulse wave observed in a certain location is presumably derived from the same pulse beat.

On the basis of the above points, the present inventor considered that the time difference between the feature point of the progressive wave component and that of the reflected wave component can be regarded as the pulse wave propagation time, and has reached the present invention.

Figure 1:
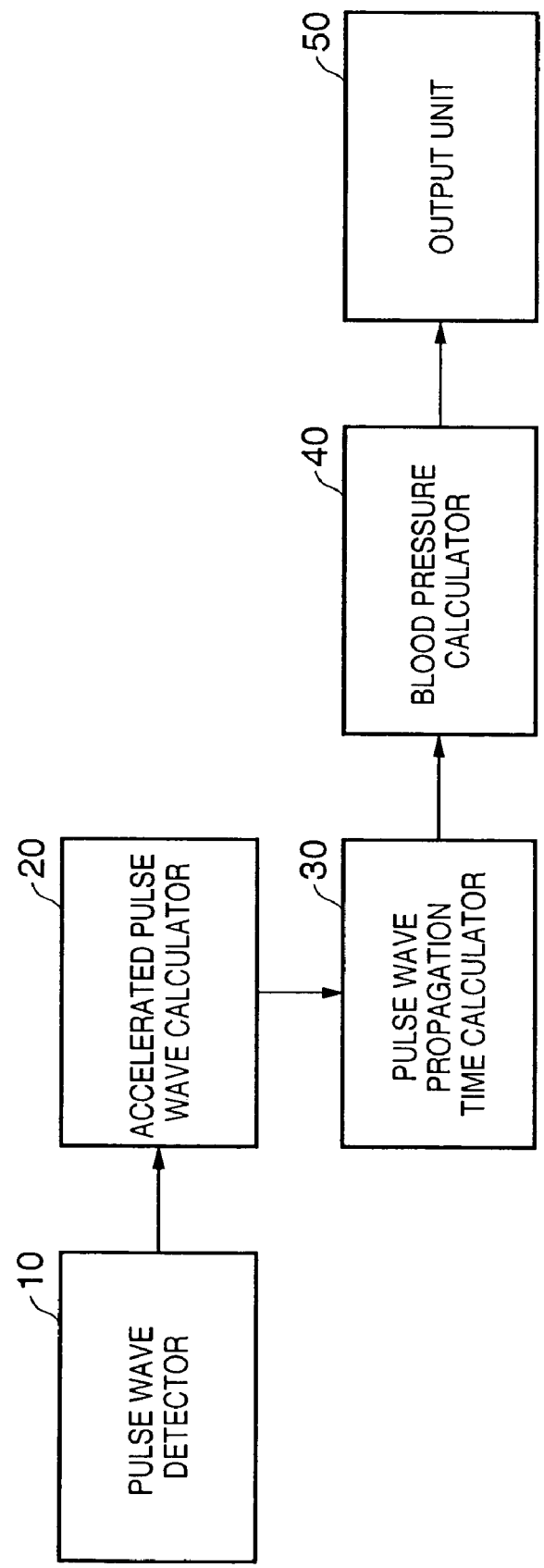
FIG. 1 is a block diagram showing an example of the arrangement of blood pressure measuring apparatus according to an embodiment of the present invention.

FIG. 1 is a view showing an example of the arrangement of blood pressure measuring apparatus according to the embodiment of the present invention.

Of this blood pressure measuring apparatus, a pulse wave sensor 10 detects a pulse wave in a predetermined location of a living body. As the pulse sensor 10, it is possible to use various arrangements, e.g., a photoplethysmograph for detecting a change in blood flow volume, i.e., a plethysmograph from the ratio of light absorbed by hemoglobin in the blood by using a light-emitting element and light-receiving element, a pressure sensor which extracts a pressure change as an electrical signal, and a cuff (which detects a pulse wave by pressurization to about a diastolic pressure).

Also, a location where a pulse wave is to be detected by attaching the pulse wave sensor 10 can be generally any arbitrary location where a pulse wave can be noninvasively detected. Examples are a fingertip, the forehead, and a location where the radial artery or carotid artery can be found.

An accelerated pulse wave calculator 20 functions as a means for extracting the progressive wave component and reflected wave component from a pulse wave. The progressive wave component and reflected wave component can be extracted from a pulse wave obtaining the accelerated pulse wave by calculating the second derivative of the pulse wave signal detected by the pulse wave sensor 10. This is described in, e.g., Iketani et al., "Photoplethysmogram (Accelerated Pulse Wave) for Evaluating Degree of Arteriosclerosis by Hypertension", Blood Pressure, vol. 10, no. 6, 2003, pp. 54-60. Note that the progressive wave component and reflected wave component may also be extracted by another method.

A pulse wave propagation time calculator 30 calculates, as the pulse wave propagation time, a time difference between a waveform presumably reflecting the progressive wave component and a waveform presumably reflecting the reflected wave component, of the characteristic waveforms contained in the accelerated pulse wave. Blood pressure calculator 40 calculates blood pressure by applying the calculated pulse wave propagation time to an expression having precalibrated coefficients. An output unit 50 is an output device such as a display, loudspeaker, or printer, and outputs the blood pressure calculated by the blood pressure calculator. Note that the calculated blood pressure may also be recorded on a recording medium such as a hard disk, or output to an external apparatus via an interface (not shown).

In this embodiment as described above, the pulse wave propagation time calculator 30 calculates the pulse wave propagation time as the time difference between the progressive wave component and the reflected wave component, by using the fact that the waveform appearing in the accelerated pulse wave obtained by calculating second-order differential of a pulse wave is divided into the progressive wave component and reflected wave component.

Figure 2:
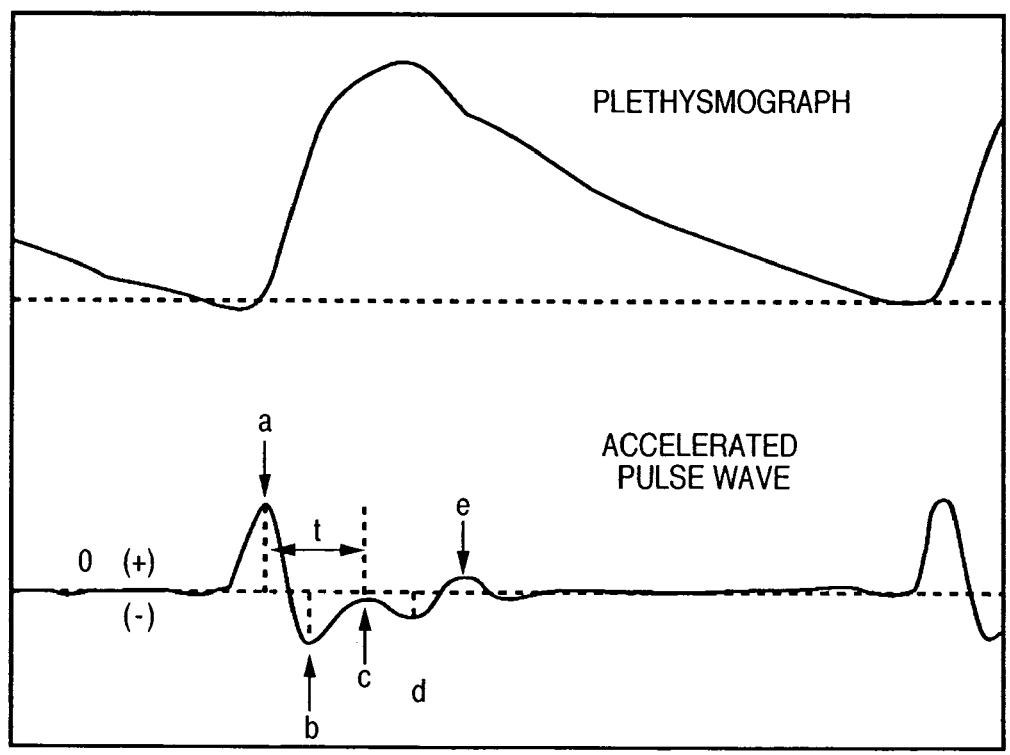
FIG. 2 is a graph showing examples of an original waveform and its accelerated pulse wave.

More specifically, a-wave to e-wave appearing in the accelerated pulse wave obtained from the original waveform shown in FIG. 2 are detected. Since a-wave and b-wave are progressive wave components and c-wave and d-wave are reflected wave components, a time difference between the timings at which these waves appear is calculated. This time difference can be obtained as a time difference between the feature points of these waveforms, e.g., the peak values. The time difference thus obtained is a time difference between pulse waves, and hence does not contain the influence of the preelection period which is contained when an ECG is used instead of one pulse wave.

Although a time difference can be calculated for each of combinations of a-wave and c-wave, a-wave and d-wave, b-wave and c-wave, and b-wave and d-wave, a time difference t between a-wave and c-wave by which the most favorable result is presently obtained is calculated as the pulse wave propagation time in this embodiment. However, it is also possible to use another combination. In addition, another value may also be used as long as the value is related to the time difference between the progressive wave component and the reflected wave component. An example is the difference between the intermediate time between the times at which the peak values of a-wave and b-wave are obtained, and the intermediate time between the times at which the peak values of c-wave and d-wave are obtained.

As the expression for calculating the blood pressure from the pulse wave propagation time, it is possible to use Blood pressure=α(pulse wave propagation time [msec])+β

($\alpha$ and $\beta$ are coefficients, $\alpha<0$, $\beta>0$)

as disclosed in, e.g., Japanese Patent Laid-Open No. 10-66681.

Note that the coefficients $\alpha$ and $\beta$ need only be determined in advance. That is, this equation is a linear equation with two unknowns, so the values of the coefficients $\alpha$ and $\beta$ can be determined by using at least two actually measured blood pressures and the corresponding pulse wave propagation times.

Each coefficient need not be fixed but may also be updated to an optimum value by using an actually measured value obtained by another method (cuff measurement or direct measurement) and the pulse wave propagation time at the corresponding timing. This actually measured value can be acquired from another apparatus, or, when the function of the blood pressure measuring apparatus of this embodiment is installed in a monitoring apparatus or the like, can be the value of periodic blood pressure measurement which the monitoring apparatus normally performs.

Figure 3:
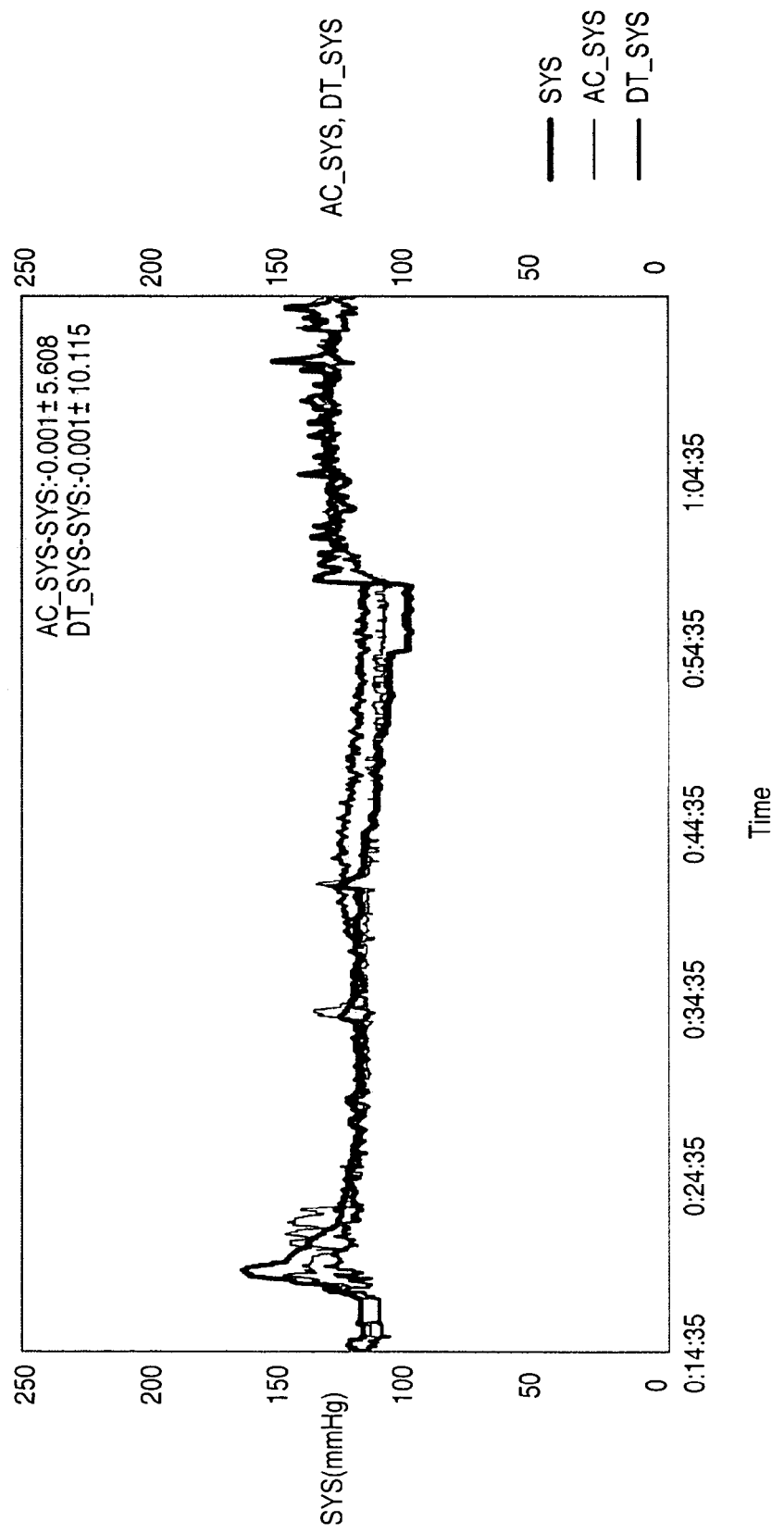
FIG. 3 is a graph showing actual examples of blood pressure obtained by the blood pressure measuring apparatus according to the embodiment of the present invention, blood pressure obtained by a conventional method, and a direct blood pressure obtained invasively.

FIG. 3 is a graph showing actual examples of blood pressures continuously calculated by the blood pressure measuring apparatus of this embodiment. Referring to FIG. 3, AC_SYS indicates blood pressure (highest blood pressure) calculated by using, as the pulse wave propagation time, the time difference between a-wave and c-wave of an accelerated pulse wave obtained by calculating second-order differential of a plethysmograph. DT_SYS indicates blood pressure similarly calculated on the basis of a pulse wave propagation time which is calculated on the basis of a plethysmograph and ECG. SYS indicates a direct blood pressure obtained invasively.

Figure 4:
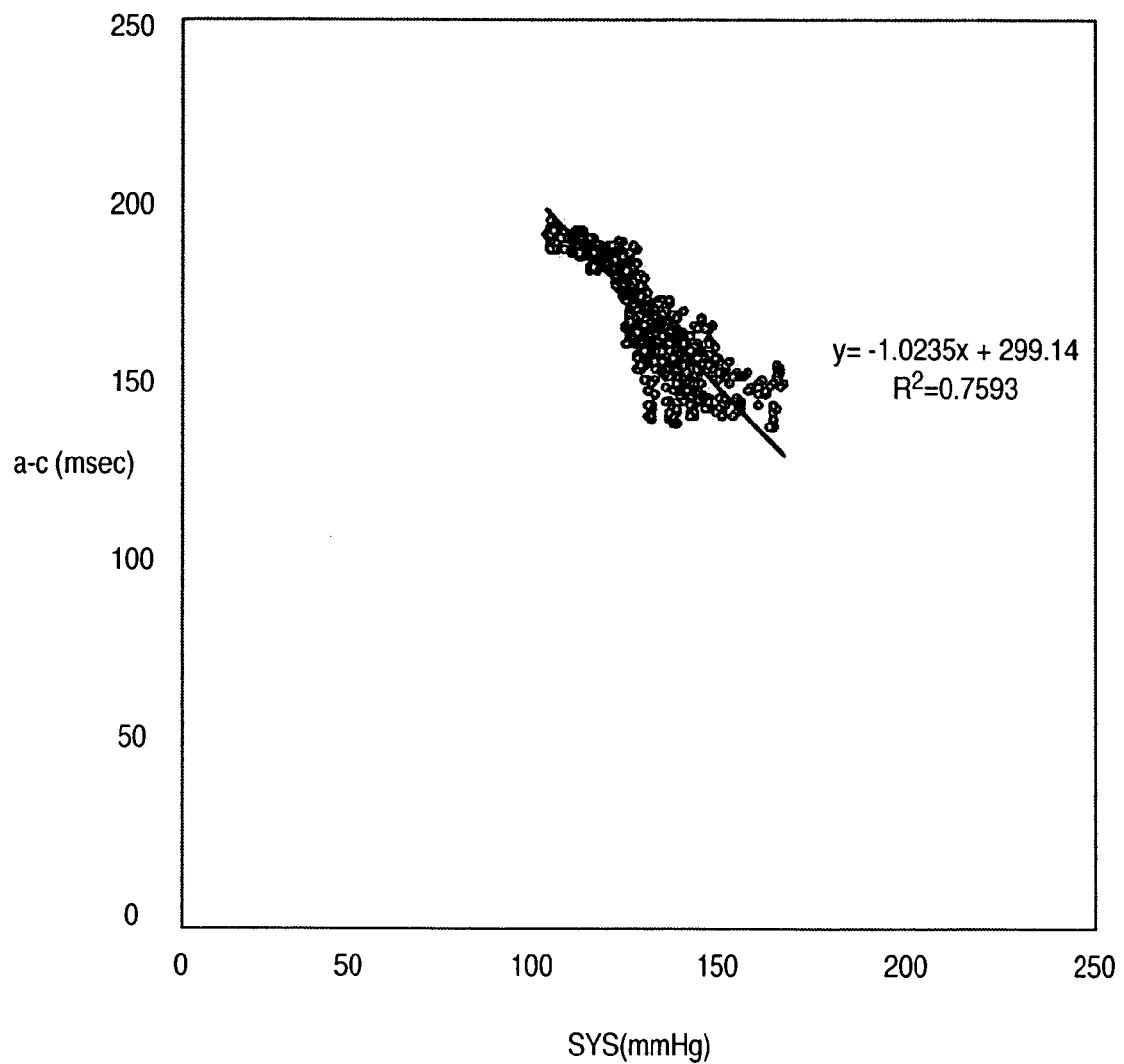
FIG. 4 is a scatter diagram showing the correlation between the blood pressure calculated by the blood pressure measuring apparatus according to the embodiment and the direct blood pressure obtained invasively.
Figure 5:
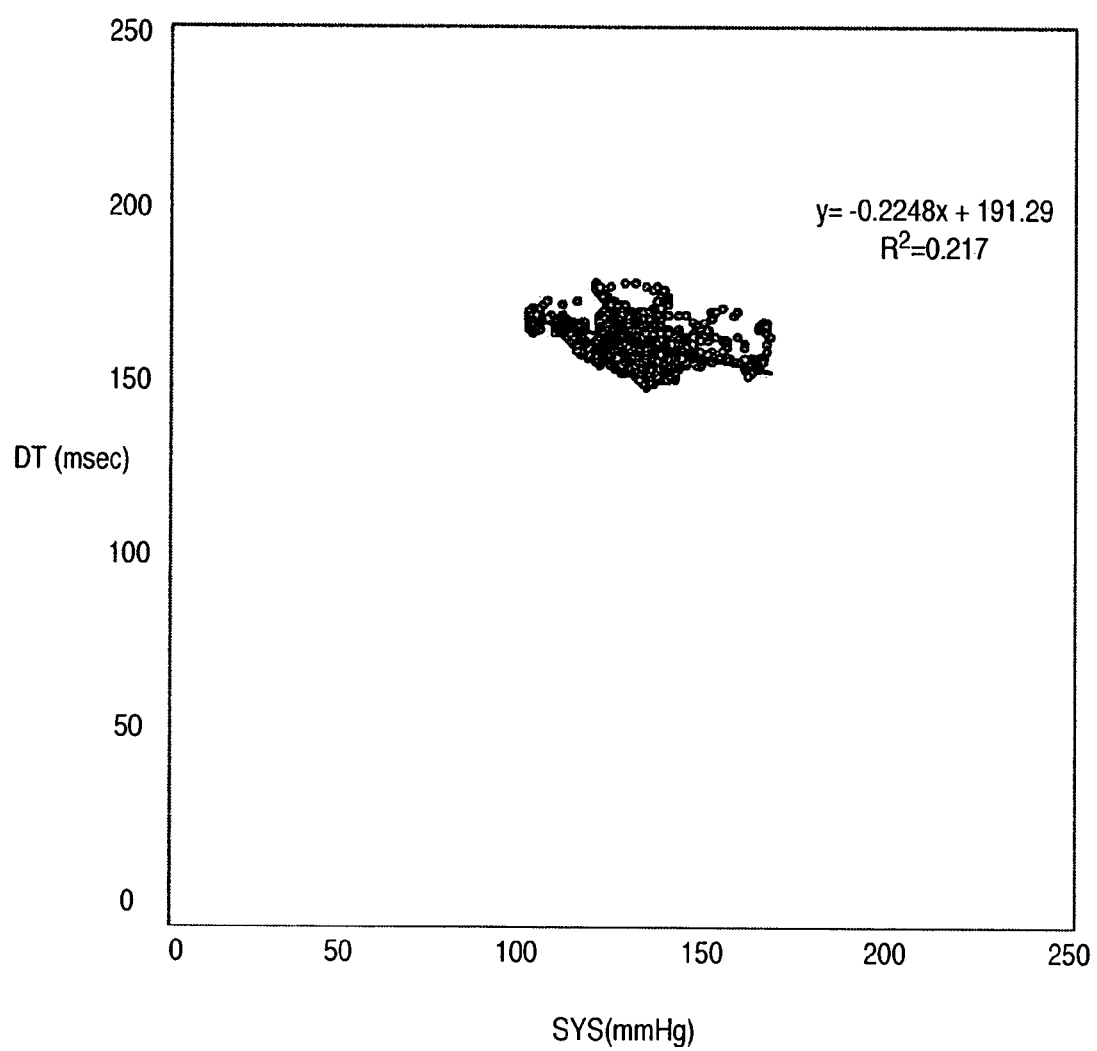
FIG. 5 is a scatter diagram showing the correlation between the blood pressure calculated by the conventional method and the direct blood pressure obtained invasively.

FIGS. 4 and 5 are scattered diagrams respectively showing the correlation between AC_SYS and SYS and the correlation between DT_SYS and SYS shown in FIG. 3.

As shown in FIGS. 3 to 5, the correlation between the actual blood pressure and the blood pressure calculated by the blood pressure measuring apparatus of this embodiment is much higher than that between the actual blood pressure and the blood pressure calculated by the conventional method combining an ECG and plethysmograph. That is, accurate values are obtained, and the trackability or compliance to blood pressure fluctuations is also high.

In this embodiment as has been explained above, the blood pressure can be obtained by using a pulse wave measured in one location such as a fingertip. Therefore, the measurement is very simple, the load on a patient is light, and continuous blood pressure calculation is possible. Also, the propagation time is obtained by using only a pulse wave, so the accuracy is higher than that of a method using an ECG. In addition, the use of a pulse wave which is a biological signal normally measured by a general biological information measuring apparatus such as a biological information monitor makes it unnecessary to add any special apparatus. Furthermore, the signal processing can be implemented by software, and hence can be readily installed as a function of the conventionally existing apparatus.

Note that when the blood pressure measuring apparatus of this embodiment is incorporated into a biological information monitoring apparatus which continuously measures, e.g., an ECG, respiration, blood oxygen saturation degree (SPO2), and pulse wave, and also periodically measures blood pressure by using a cuff, the operation of the biological information monitoring apparatus may also be controlled on the basis of the calculated blood pressure.

That is, blood pressure measurement using a cuff requires avascularization, and hence can be performed only at a predetermined interval. However, it is desirable to immediately perform cuff blood pressure measurement if, for example, the condition of a patient has abruptly changed. Therefore, if the blood pressure always calculated by the blood pressure measuring apparatus of this embodiment is continuously larger than a predetermined upper limit or smaller than a predetermined lower limit for a predetermined time, a cuff is activated to start measuring the blood pressure, or an alarm is output. This makes it possible to increase the usefulness of the biological information monitoring apparatus.

As many apparently widely different embodiments of the present invention can be made without departing from the spirit and scope thereof, it is to be understood that the invention is not limited to the specific embodiments thereof except as defined in the appended claims.

What is claimed is:

1. Blood pressure measuring apparatus comprising:
   pulse wave detecting unit adapted to detect a pulse wave in a predetermined location of a living body;
   extracting unit adapted to extract a progressive wave component and a reflected wave component contained in the pulse wave;
   pulse wave propagation time calculating unit adapted to calculate a pulse wave propagation time from the progressive wave component and the reflected wave component; and
   blood pressure calculating unit adapted to calculate blood pressure on the basis of the pulse wave propagation time.

2. The apparatus according to claim 1, wherein said extracting unit generates an accelerated pulse wave by calculating second-order differential of the pulse wave.

3. The apparatus according to claim 2, wherein said pulse wave propagation time calculating unit calculates the pulse wave propagation time by using a-wave and b-wave contained in the accelerated pulse wave as the progressive wave component, and c-wave and d-wave contained in the accelerated pulse wave as the reflected wave component.

4. The apparatus according to claim 3, wherein said pulse wave propagation time calculating unit calculates, as the pulse wave propagation time, a time difference between one of a-wave and b-wave and one of c-wave and d-wave contained in the accelerated pulse wave.

5. The apparatus according to claim 1, wherein said pulse wave detecting unit detects a plethysmograph as the pulse wave.

6. The apparatus according to claim 1, wherein said blood pressure calculating unit calculates the blood pressure by applying the pulse wave propagation time to $$\text{Blood pressure} = \alpha \times \text{pulse wave propagation time} + \beta$$

(where $\alpha$ and $\beta$ are coefficients).

7. The apparatus according to claim 6, further comprising updating unit adapted to update the coefficients contained in the equation by using blood pressure of the living body measured by another method, and the blood pressure calculated by said blood pressure calculating unit.

8. The apparatus according to claim 7, wherein the blood pressure measured by said another method is one of blood pressure measured using a cuff and a direct blood pressure obtained invasively.

9. A biological information monitoring apparatus comprising blood pressure measuring apparatus cited in claim 1.

10. The apparatus according to claim 9, wherein the blood pressure calculated by said blood pressure calculating unit is used as a condition for starting cuff blood pressure measurement.

* * * * *